(12) United States Patent
Fan et al.

(10) Patent No.: US 6,391,463 B1
(45) Date of Patent: *May 21, 2002

(54) SILICON-CONTAINING ALKOXYLATED (METH)ACRYLATE MONOMERS

(75) Inventors: Mingxin Fan, West Chester; Gary W. Ceska, Exton; James Horgan, West Chester; Thomas Hazell, Exton, all of PA (US)

(73) Assignee: Sartomer Technology Co., Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/772,980

(22) Filed: Dec. 23, 1996

(51) Int. Cl.$^7$ ................................. C08F 30/08
(52) U.S. Cl. ................. 428/447; 556/445; 526/279; 522/172
(58) Field of Search ................. 556/445; 428/447; 526/279; 522/172

(56) References Cited

U.S. PATENT DOCUMENTS

| | | | | |
|---|---|---|---|---|
| 4,440,850 A | * | 4/1984 | Paul et al. ................. | 430/325 |
| 4,468,524 A | * | 8/1984 | Zahir et al. ................ | 560/221 |
| 4,602,074 A | | 7/1986 | Mizutani et al. ........... | 526/245 |
| 4,716,091 A | | 12/1987 | Yoshihara et al. .......... | 430/66 |
| 4,743,667 A | | 5/1988 | Mitzutani et al. .......... | 526/245 |
| 5,017,668 A | * | 5/1991 | Yoshihoka et al. ......... | 526/279 |
| 5,717,125 A | | 2/1998 | Wolter et al. .............. | 556/438 |
| 5,736,747 A | * | 4/1998 | Thurber et al. ........ | 252/182.12 |

FOREIGN PATENT DOCUMENTS

| | | |
|---|---|---|
| JP | 1-292018 | * 11/1989 |
| JP | 2-33338 | * 5/1990 |
| JP | 2-133338 | 5/1990 |
| JP | 2-156246 | 6/1990 |
| JP | 2-269112 | 11/1990 |
| WO | WO 96/12749 | 5/1996 |

OTHER PUBLICATIONS

Plueddemann, Edwin P. "Bonding Through Coupling Agents", Polymer Preprints, vol. 24, 196–7, Mar. 1983.*

* cited by examiner

*Primary Examiner*—Margaret G. Moore
(74) *Attorney, Agent, or Firm*—Michael B. Fein; Cozen O'Connor

(57) ABSTRACT

Compounds of the formula

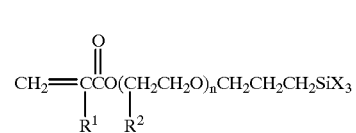

(I)

wherein
$R_1$=H, $CH_3$
$R_2$=H, $CH_3$, $CH_2CH_3$, or $CH_2CH_2CH_3$
n=1–10
X=halogen, ($C_1$–$C_6$) alkyl, ($C_1$–$C_6$) alkoxy, or aromatic radical are shown to be useful as coupling agents or adhesion promotors in free radically curable compositions such as UV curable and peroxide curable (meth) acrylate based coating compositions. The associated methods, curable compositions, coatings, adhesives and coated articles are also disclosed.

19 Claims, No Drawings

SILICON-CONTAINING ALKOXYLATED (METH)ACRYLATE MONOMERS

FIELD OF THE INVENTION

This invention relates to silicon-containing (meth)acrylate monomers which are useful as coupling agents or adhesion promoters in free radically curable compositions such as UV curable and peroxide curable (meth)acrylate-based coating Compositions.

DESCRIPTION OF THE PRIOR ART

In the past 20 years, radiation curing has become more and more popular since it provides low or zero volume emission and high productivity. This new technology has been widely used in coatings, inks and adhesives. Radiation curable compositions are typically mixtures of monomers, oligomers, photoinitiators, or additives which are applied to the substrates and cured in place via ultraviolet light. The adhesion between the substrates and the cured compositions varies from system to system. Various additives have been used to improve adhesion. Silane agents have been widely used to improve adhesion in traditional coatings and composites based on epoxy chemistry. However, the application and selection of silane agents depends on cure mechanisms. In the radiation curable case, only one compound, gamma-methacryloxypropyl trimethoxysilane, is compatible with the cure mechanism and available.

Gamma-methacryloxypropyl trimethoxysilane monomer is a well known commercially available coupling agent for bonding coatings to substrates. The coupling agent is mixed with other copolymerizable monomers such as (meth) acrylates, i.e., acrylates, methacrylates, or mixtures thereof, and the mixture of monomers is applied to a surface and cured.

The methacryloxypropyl trimethoxysilane coupling agent of the prior art is prepared from allylmethacrylate, a volatile and odorous compound. The presence of the allylmethacrylate starting material along with the methacryloxypropyl trimethoxysilane monomer coupling agent also causes odor problems with the cured coatings. Other silane-based coupling agents are available, but are mainly directed to two-part, non-(meth)acrylate systems. See Waldman, *Silane Coupling Agents Improve Performance*, Modern Paints and Coatings, February, 1996.

PCT publication WO 96/12749 of May 2, 1996 shows silane oligomers and radiation curable coating compositions for optical fiber coating. The silane oligomers are high in molecular weight (500–11,000) and a high level of silane oligomer is needed, typically about 5–99% of the coating composition. These silane oligomers are typically prepared based on urethane chemistry and urethane linkage.

Derwent abstract 95-225640/30 relating to DE-4416857 of Jun. 29, 1995 shows hydrolysable and polymerisable silane(s) useful in coating, adhesive, and moulding compositions and composites prepared from reactive silane and unsaturated compound and polycondensed to hetero polysilicic acid compound or polymerized. These silanes have carboxylic acid functional groups for use in the radiation-hardenable binders. These silane agents are prepared from hydroxy containing compounds and acid anhydride containing silanes.

SUMMARY OF THE INVENTION

It is an object of this invention to provide coupling agents which have reduced volatility and odor.

It is another object to provide coupling agents which match the adhesion performance of the prior coupling agents, but avoid the volatility and odor problems.

A further object is to provide improved UV curable coating compositions which have reduced volatility and odor.

These objects, and others as will become apparent from the following disclosure, are achieved by the present invention which comprises in one aspect compounds of the formula

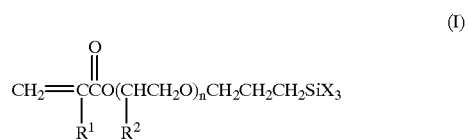

wherein
$R_1$=H, $CH_3$
$R_2$=H, $CH_3$, $CH_2CH_3$, or $CH_2CH_2CH_3$
n=1–10
X=halogen, ($C_1$–$C_6$) alkyl, ($C_1$–$C_6$) alkoxy, or aromatic radical, wherein each of the three X substituents can be the same or different.

In another aspect the invention comprises a method of making such compounds of formula I comprising reacting an alkoxylated allyl(alk)acrylate of the formula

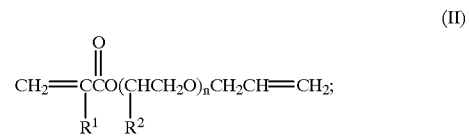

with a silane of the formula

in the presence of a transition metal catalyst.

In another aspect the invention comprises the use of the new monomer compounds in coating and adhesive compositions; the resulting coating compositions, and coated articles.

DETAILED DESCRIPTION OF THE INVENTION

The novel monomer compounds are the reaction product of a silane of the formula

and an alkoxylated(alk)acrylate of the formula

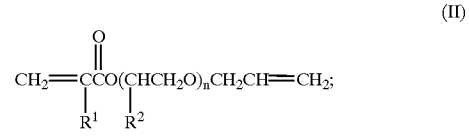

in the presence of a transition metal catalyst.

Suitable silanes of formula V include trichlorosilane, tribromosilane, trifluorosilane, trimethoxsilane, triethoxysilane, trimethylsilane, and triphenylsilane. The preferred silane is trimethoxysilane.

Suitable alkoxylated(alk)acrylates are the reaction product of alkoxylated allyl alcohol and (meth)acrylic acids. The alkoxylated allyl alcohols are prepared by reacting alkylene oxide with allyl alcohol. Suitable alkylene oxides are ethylene oxide, propylene oxide, which is preferred, butylene oxide, and pentylene oxide. The number of alkylene oxide groups, n, can be about 1 to 10, with about 2 to 5 being preferred.

Suitable (meth)acrylic acids are acrylic acid and methacrylic acid, with the latter preferred.

The transition metal catalyst is preferably platinum based, for example, $H_2PtCl_6$. Other suitable catalysts are, for example, rhodium-containing compounds.

Preferred compounds of the invention are those of formula I wherein both $R_1$ and $R_2$ are both methyl, n is about 2–5, and X is methoxy.

The monomers of the invention are preferably used in admixture with other unsaturated monomers and the mixture of monomers is applied to a surface of an article and cured to form a coating or adhesive.

The surfaces to which the coating compositions of the invention can be applied include glass, metal, wood, steel, plastic and the like. The new monomers can be used in the same manner as the prior methacryloxypropyl trimethoxysilane monomer with the advantage of imparting lower odor and having reduced volatility to the radiation curable compositions.

The amounts of the various components in the coating compositions are the radiation curable compositions may contain 05–10% of silane of this invention, 0.5–15% of photoinitiator or photoinitiator mixture, and 50–90% of (meth)acrylate monomers, oligomers or monomer/oligomer mixture. The various components can be mixed as in the regular composition and applied to the substrate surface by roller coating, spraying, or any other method. The applied coatings can be cured by irradiation with UV light. Alternatively, the silane agent could be applied first to the substrate followed by regular coating application and curing.

The following examples illustrate several embodiments of the invention.

EXAMPLE

Example 1
Synthesis of Propoxylated Allyl Methacrylate

Propoxylated allyl alcohol (5 propylene oxide units per molecule) (1344.8 g), Dow Chemical brand, methacrylic acid (448.5 g), 4-methoxyphenyl (6.75 g), methane sulfonic acid (70%, 33.75 g), and heptane (405.0 g) were added to a reactor and stored at room temperature. Air sparge was applied. Then the mixture was heated to reflux and water generated was removed via azeotrope. After the reaction was complete (no more water formation), the mixture was neutralized with 25% NaOH and washed twice with 25% NaOH. The final product, propoxylated allyl methacrylate having 5 propylene oxide units per molecule, was obtained by removing the heptane solvent under reduced pressure. Yield was 1532.4 grams.

Example 2
Synthesis of Propoxylated Allyl Methacrylate

Example 1 was repeated using having 2 propylene oxide units per molecule of propoxylated allyl alcohol, forming propoxylated allyl methacrylate having 2 propylene oxide units per molecule was obtained.

Example 3
Synthesis of Propoxylated methacryloxyproply trimethoxysilane

Monomer from Example 2 (104.0 g), trimethoxysilane (55.0 g), 4-methoxyphenol (0.16 g), platinum catalyst (4 drops, made by dissolving 2.0 g $H_2PtCl_6$ in 98.0 g isopropanol) were added to a three neck flask and stirred. After 4-methoxyphenol was dissolved, air sparge was applied and the mixture was heated to 65° C. The addition reaction took place with the observation of exotherm. The reaction was followed by FTIR with the disappearance of Si-H stretch at 2200 $cm^{-1}$. The reaction was completed in 8.0 hrs.

Example 4
Synthesis of Propoxylated Methacryloxy Propyl Triethylsilane

Example 3 was repeated using equal moles of triethylsilane. Propoxylated methacryloxy propyl triethylsilane was obtained.

While the invention has been described in great detail, various alternatives and improvements should become apparent to those skilled in this art without departing from the spirit and scope of the invention as set forth in the claims.

What is claimed is:

1. A method for improving the adhesion properties of a UV curable coating or adhesive composition comprising incorporating in said UV curable coating or adhesive composition an adhesion-promoting compound having the formula

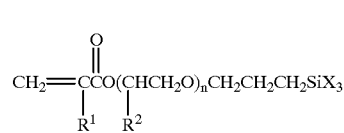

(I)

wherein
   $R_1$=H, $CH_3$
   $R_2$=H, $CH_3$, $CH_2CH_3$, or $CH_2CH_2CH_3$
   n=2–10
   X=halogen, $(C_1–C_6)$ alkyl, $(C_1–C_6)$ alkoxy, or aromatic radical, wherein each of the three X substituents can be the same or different, said UV curable coating or adhesive composition consisting essentially of said adhesion-promoting compound, one or more other unsaturated monomers, and a photoinitiator.

2. The method according to claim 1 wherein said one or more other unsaturated monomers comprise (meth)acrylate monomers.

3. The method according to claim 1 wherein said one more other unsaturated monomers comprise a mixture of monomers and oligomers.

4. The method according to claim 1 which comprises applying said UV curable coating or adhesive composition to a substrate and curing with light.

5. The method according to claim 4 which comprises applying said UV curable coating or adhesive composition to a substrate by roller coating or spraying.

6. The method according to claim 4 wherein said unsaturated monomers comprise one or more (meth)acrylate monomers.

7. The method according to claim 6 wherein said unsaturated monomers comprise a mixture of monomers and oligomers.

8. The method according to claim 1 wherein X is methoxy.

9. The method according to claim 1 wherein n is 2 to 5.

10. The method according to claim 1 wherein $R_2$ is methyl.

11. The method according to claim 10 wherein $R_1$ is methyl, n is 2 to 5, and X is methoxy.

12. A composition for UV curable coatings or adhesives consisting essentially of a mixture of an amount effective to promote adhesion to a substrate of coatings or adhesives cured from said composition of a compound of the formula

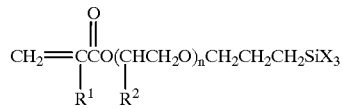

(I)

wherein $R_1$=H, $CH_3$ $R_2$=H, $CH_3$, $CH_2CH_3$, or $CH_2CH_2CH_3$ n=2–10

X=halogen, ($C_1$–$C_6$) alkyl, ($C_1$–$C_6$) alkoxy, or aromatic radical, wherein each of the three X substituents can be the same or different;

one or more other unsaturated monomers, and a photoinitiailor.

13. The composition according to claim 12 wherein said monomers or oligomers comprise (meth)acrylates.

14. The composition according to claim 12 wherein said unsaturated monomers comprise a mixture of monomers and oligomers.

15. The composition according to claim 12 wherein X is methcoxy.

16. The composition according to claim 12 wherein n is 2 to 5.

17. The composition according to claim 12 wherein $R_2$ is methyl.

18. The composition according to claim 12 wherein $R_1$ is methyl, n is 2 to 5, and X is methoxy.

19. An article comprising glass, metal, wood, steel, or plastic coated with the UV curable coating or adhesive composition of claim 12.

* * * * *